United States Patent [19]
Lee et al.

[11] Patent Number: 6,033,582
[45] Date of Patent: Mar. 7, 2000

[54] SURFACE MODIFICATION OF MEDICAL IMPLANTS

[75] Inventors: Dosuk D. Lee, Brookline; Atul Nagras, Somerville; Pramod Chakravarthy, Arlington; Anthony M. Majahad, Cambridge, all of Mass.

[73] Assignee: Etex Corporation, Cambridge, Mass.

[21] Appl. No.: 09/008,650

[22] Filed: Jan. 16, 1998

Related U.S. Application Data

[63] Continuation-in-part of application No. 08/786,869, Jan. 22, 1997, which is a continuation-in-part of application No. 08/589,409, Jan. 22, 1996, Pat. No. 5,843,289.

[51] Int. Cl.$^7$ ...................................................... B44C 1/22
[52] U.S. Cl. ................................. 216/37; 216/67; 216/77; 204/192.32; 204/192.35
[58] Field of Search .................................. 216/75, 77, 78, 216/67, 37; 204/192.32, 192.35

[56] References Cited

U.S. PATENT DOCUMENTS

| | | | |
|---|---|---|---|
| 3,852,045 | 12/1974 | Wheeler et al. | 29/182 |
| 3,905,777 | 9/1975 | Lacroix | 29/183.5 |
| 3,994,793 | 11/1976 | Harvilchuck et al. | 204/192 |
| 4,203,800 | 5/1980 | Kitcher et al. | 156/643 |
| 4,533,272 | 8/1985 | Mears | 623/1 |
| 4,542,539 | 9/1985 | Rowe, Jr. et al. | 623/16 |
| 4,547,260 | 10/1985 | Takada et al. | 156/643 |
| 4,644,942 | 2/1987 | Sump | 623/16 |
| 4,654,314 | 3/1987 | Takagi et al. | 501/82 |
| 4,659,331 | 4/1987 | Matthews et al. | 623/20 |
| 4,743,256 | 5/1988 | Brantigan | 623/17 |
| 4,790,851 | 12/1988 | Suire et al. | 623/16 |
| 4,865,603 | 9/1989 | Noiles | 623/18 |
| 5,164,331 | 11/1992 | Lin et al. | 437/192 |
| 5,176,792 | 1/1993 | Fullowan et al. | 156/652 |
| 5,246,530 | 9/1993 | Bugle et al. | 156/643 |
| 5,258,098 | 11/1993 | Wagner et al. | 156/645 |
| 5,260,093 | 11/1993 | Kamel et al. | 427/2 |
| 5,282,861 | 2/1994 | Kaplan | 623/16 |
| 5,354,416 | 10/1994 | Okudaira et al. | 156/643 |
| 5,380,547 | 1/1995 | Higgins | 427/2.26 |
| 5,531,862 | 7/1996 | Otsubo et al. | 156/643.1 |
| 5,843,289 | 12/1998 | Lee et al. | 204/192.3 |

FOREIGN PATENT DOCUMENTS

| | | |
|---|---|---|
| 0 388 576 | 9/1990 | European Pat. Off. . |
| 0 447 744 A2 | 9/1991 | European Pat. Off. . |
| 42 06 490 | 9/1993 | Germany . |
| WO 86/06617 | 11/1986 | WIPO . |
| WO 94/25637 | 11/1994 | WIPO . |

OTHER PUBLICATIONS

Oehrlein, et al., "Mechanism of Silicon Surface Roughening by Reactive Ion Etching", Surface and Interface Analysis 8:243 (1986).

Hartney, et al., "Oxygen Plasma Etching for Resist Stripping and Multilayer Lithography", J. Vac. Sci. Technol. B7 (1): (Jan./Feb. 1989).

G.S. Oehrlein, Handbook of Plasma Processing Technology. Ch. 8 Reactive Ion Etching.

*Primary Examiner*—Randy Gulakowski
*Assistant Examiner*—Shamim Ahmed
*Attorney, Agent, or Firm*—Clark & Elbing LLP; Mary Rose Scozzafava

[57] ABSTRACT

An irregularly etched medical implant device is provided having random non-uniform relief patterns on the surface ranging from about 0.3 μm to less than about 20 μm in depth. The random, irregular surface as defined by the etch micromorphology and respective dimensional properties are obtained by exposing a surface to a reactive plasma in a chamber wherein said reactive plasma produces a reaction product with the surface to thereby etch the surface, said reaction product or a complex thereof having a vapor pressure lower than a pressure in the chamber; providing a dynamic masking agent during the etching process; and removing the reaction products.

29 Claims, 4 Drawing Sheets

SURFACE MODIFICATION OF MEDICAL IMPLANTS

This application is a continuation-in-part application of U.S. patent application Ser. No. 08/786,869 filed Jan. 22, 1997 and similarly entitled "Surface Modification of Medical Implants", which is a continuation-in-part application of U.S. patent application Ser. No. 08/589,409, filed Jan. 22, 1996 and similarly entitled "Surface Modification for Medical Implants now U.S. Pat. No. 5,843,289, which are hereby incorporated in its entirety by reference.

FIELD OF INVENTION

This invention relates to methods for surface modifications of articles made of various materials (e.g., metals, polymers, and ceramics), such as medical implant devices (e.g., vascular grafts, orthopedic prostheses, and heart valves). Specifically, the invention relates to treatment of implant device surfaces to obtain desirable surface features that enhance and optimize adhesion of coating materials and/or tissue interactions with the surface of a medical implant device.

BACKGROUND OF THE INVENTION

Diseased and damaged parts of the body are best repaired or replaced with an organism's own tissue. Physicians and surgeons routinely replace tissue, organs or bone through delicate and complicated medical procedures. Appropriate donor tissues are generally procured elsewhere: either from the recipient's own body (autograft); from a second donor (allograft); or, in some cases, from a donor of another species (xenograft). Tissue transplantation is costly, and suffers from significant failure rates, an increasing risk of disease transmission and inadequate supplies of donor tissues. Therefore, in response to these current transplantation issues, use of artificial or synthetic medical implant devices, fabricated through tissue engineering technology, has been the subject of considerable attention.

Although implant devices can be used in some instances as an alternative to donor-based transplants, they too often produce unsatisfactory results because of the implant's incompatibility with the body and inability to function properly. For example, polymeric vascular graft inner-wall surfaces are not usually adhesive enough to completely prevent cellular or other bioactive coatings from unwanted migration along the blood vessel's inner-wall surface. Lack of cellular adhesion to the vascular graft's synthetic surface sets-up conditions that increase the risk of thrombosis, hyperplasia and other medical/surgical procedural complications. Vascular grafts require non-thrombogenic surfaces. Vascular implant materials must have a biocompatible surface, allowing only a minimal response of platelets to the vessel's inner surface; and, at the same time, have the correct fluid dynamics at the vessel wall-blood interface to eliminate or reduce unwanted turbulence and eddy formation. In other types of implants, unwanted fibrogenesis can occur, encasing the implant. The implant will then have an increased risk of rejection and other medical complications. Thus, efforts have been directed at application of biocompatible coatings, such as Teflon, onto implant surfaces.

Materials from which implant devices are made (e.g., metals and polymers) are often not manufactured with surface conditions conducive to optimal functionality (e.g., adhering biocompatible materials, cellular coatings or host tissue); they require some form of conditioning and/or pretreatment that will physically enhance the surface to promote its adhesive properties to the desired tissue or coating material.

Conventional methods for surface treatment include physical, chemical or electrochemical techniques. Surface modification with physical techniques can be achieved with abrasives, such as found in sand blasting which produces macroporous surfaces, or machining with equipment, such as milling machines that also produce macro pores but require an expensive operation. Heat treatment of surfaces is another physical method used to anneal, harden or smooth metals. Traditional metal chemical modification of a surface uses wet methods in processes such as acid etching, "pickling," and electrochemical passivation. Chemically treated surfaces typically are not desirable for use a cellular growth surfaces because of the presence of unwanted byproducts of the chemical process such as hydride layers remaining on the surface. Polymer chemical surface modifications generally involve cleaning procedures with aqueous and/or organic solvents; some machining techniques also have been used to modify polymeric surfaces, as well as heat treatment.

Electrochemical surface modification includes electroplating of materials such as nickel, copper, chrome, titanium, precious metals and/or other commonly used plating metal and metallic compounds. Other surface treatments include conventional coating techniques (i.e., spray painting, dipping, etc.) as well as vapor deposition and plasma grafting technologies. Comprehensive descriptions of the art of traditional surface treatment and finishing can be found in *A Guide to Metal and Plastic Finishing* (Maroney, Marion L.; 1991), *Handbook of Semiconductor Electrodeposition* (*Applied Physics,* 5) (Pandey, R. K., et. al.; 1996), *Surface Finishing Systems: Metal and Non-Metal Finishing Handbook-Guide* (Rudzki, George J.; 1984), and *Materials and Processes for Surface and Interface Engineering* (*NATO Asi Series. Series E, Applied Sciences,* 115) (Pauleau, Ives (Editor); 1995); herein incorporated by reference.

Cold plasmas have been used to process materials for a variety of technologies, such as metallurgy, microelectronics, and biotechnology. Plasma applications include the treatment of solid surfaces, deposition of films, surface modifications and/or dry etching of surface layers.

Plasmas are created when a sufficient amount of energy, higher than the ionization energy, is added to gaseous atoms and/or molecules, causing ionization and subsequently generating free electrons, photons, free radicals and ionic species. Often referred to as a fourth state of matter, plasmas do not exhibit the same type of phase changes as other states of matter [e.g., solid to liquid (melting), gas to liquid (condensation), or solid to gas (sublimation)]. Transition of a gas (or vapor) from an unexcited, electrically stable state to an ionized plasma state tends to occur through a continuous process rather than a distinct phase change. The excitation energy supplied to a gas to form a cold plasma can originate from electrical discharges, direct currents, radio frequencies, microwaves or other forms of electromagnetic radiation. Plasmas are characterized by the following parameters: density of neutral particles, densities of electrons and ions, energy distributions, and the degree of ionization used to pseudo-quantify charge species density.

Plasma techniques for modifying the surface characteristics of many materials are known. Specific applications for surface modified materials have been described for both microcircuit and medical implant device technology. Plasma dry etching processes are routinely used in the semiconductor and microelectronics industries. Those industries generally use plasma dry etching techniques in which unmasked regions are subjected to a clean etch utilizing relatively high power-to-surface-area ratios, ultra-low pressures and pristine conditions that result in an absence of extrinsic molecules. These conditions are used to produce a smooth, minimally defective planar surfaces. Additionally, microcircuit etching requires precise and defined etch patterns and therefore employs static masking techniques in the plasma dry etching process.

Oehrlein et al in *Surface Interface Anal.* 8:243 (1986) investigate the mechanism of surface roughening observed in the microelectronics industry on silicon surfaces. Oehrlein reports surface features on the order of 80 nm to 330 nm. Although Oehrlein suggests non-uniform etch rates due to involatile surface residues as the source of the surface roughness, the scale of the roughness was much less than those deem desirable in medical implant applications. This is because for the chosen target and gas used, the etch time used was insufficient to generate an etch depth deeper than 300 nm. Furthermore, Oehrlein teaches etches deeper than 300 nm are undesirable.

In the medical implant industry, the use of plasma treatment of materials has generally been confined to surface conditioning without significant attention of the surface morphology. Descriptions and elaboration of surface modifications for implants and other devices by RF plasmas can be found in the following sources and herein are incorporated by reference: U.S. Pat. Nos. 3,814,983; 4,929,319; 4,948,628; 5,055,316; 5,080,924; 5,084,151; 5,217,743; 5,229,172; 5,246,451; 5,260,093; 5,262,097; 5,364,662; 5,451,428; 5,476,509; and 5,543,019.

Many plasma treatment techniques, for polymers in particular, use cold plasmas to activate the surface by plasma-induced polymerization and/or RF plasma treatment to break surface polymer bonds. This action generates ions and free radicals, setting up favorable conditions for subsequent RF plasma-induced polymerization and grafting of monomers to the substrate surface as described in U.S. Pat. No. 5,080,924; incorporated herein by reference. In another application, similar covalent bonding of polymeric biocompatible materials onto intraocular lenses via RF plasma grafting was successfully achieved, creating a microscopically smooth surface as described in U.S. Pat. No. 5,260,093; herein incorporated in reference.

There is then, a need to modify implant substrate material surfaces so that these medical devices have the appropriate roughness, porosity and texture necessary to affix inorganic, polymeric and/or biological coatings and allow cellular in-growth into the device surface.

BRIEF DESCRIPTION OF THE DRAWING

The invention is described with reference to the figures which are presented for the purpose of illustration only and which are in no way limiting of the invention and in which.

SUMMARY OF THE INVENTION

The present invention is intended to provide roughened surfaces that have varied morphologies that exhibit non-uniform pitting and porosity; all of which are characteristics needed for reliable and functional adhesion of materials to implant surfaces. Plasma etching in conjunction with a dynamic masking function produces the irregularly roughened surfaces of the invention. The inventive method's use of the appropriate plasma gases and plasma operating conditions is capable of etching a medical implant device's substrate surface with distinctive morphologies.

The inventive process is based on specific sequences of procedures that utilize specific combinations of inert and reactive gases, contingent on the material to be processed. The gases must be capable of creating a plasma. The RF plasma, when appropriately generated and preferably in conjunction with a dynamic masking process, will etch surfaces of materials to be used in the fabrication of medical implant devices. The surface of an implant will be modified in such a way as to enhance the surface morphology thereby making it more favorable in applications that require specific surface configurations, such as increased surface area to base area ratios while exhibiting the same substrate material density. This in turn provides the appropriate roughness and texture that will yield desirable adhesion attributes for improved coating with biocompatible materials and/or set-up conditions that will promote appropriate physiological responses in the body.

The invention uses radio frequency (RF) generated cold plasmas in the presence of inert gases and/or reactive gases sustained in a reaction chamber to modify and micro-sculpt surfaces of articles such as medical devices designed for implantation in the human body. The inventive method achieves surface modification effects through the dry, chemical etching action of plasma particles. Etching occurs through chemical reactions between reactive plasma species and the sample surface to produce reaction products which are removed from the system either as volatile reaction products or complexed with other agents (e.g., water vapor). In some instances, plasma particles can cause the physical ejection of one or more of the surface molecules from the surface, also known as sputtering; some of which may be re-deposited back onto the surface, as a solid, in a different physical configuration.

In one embodiment of the invention, where an inert gas, such as helium or argon, is mixed with a reactive gas, relative concentrations between the inert and reactive gases may be adjusted to afford one means of control of etching rates.

In preferred embodiments of the present invention, a reactive plasma etching process is employed to modify the surface of an article such that the resulting roughness, porosity and texture are optimized for application of a coating, or coatings. In another embodiment, the invention is used to produce a roughened surface morphology to enhance cellular in-growth activity and adhesion to the surface.

In general, the article to be etched will be composed of one, or a combination of, metallic, ceramic, polymeric, and/or naturally occurring solid-surfaced materials. The inventive method cannot be applied to liquid or gaseous materials.

A preferred embodiment for the invention's surface etching method uses a generated plasma, housed in a chamber capable of sustaining the plasma at low pressures and with the capability to vary the plasma gas flow rates. The inventive method exposes an article's surface to a plasma that is comprised of active etching species and, in some embodiments, sputtering ions that effect a "non-uniform etch rate" and "non-uniform sputter rate," respectively.

In general, the inventive method utilizes a low-power-to-surface-area, radio frequency generated plasma operated at relatively low vacuums as compared to the high power levels and ultra-low pressures commonly used in the semiconductor industry. The inventive method plasma frequently employs the use of contaminant or extrinsic species that may or may not be reactive with the target but which also, in some way, promotes an integrated interaction with the target and the plasma. These extrinsic species originate from the reaction chamber wall residues, the weak vacuum conditions and residual atmospheric substances. Plasma contaminants may include water vapor, carbon dioxide, dust/particulates, and/or sputter ions from target holder materials, chamber walls or specific sputtering targets as described in Example 4.

The presence of extrinsic species during the etching process results in irregular etching. The irregular etching may be due to random local fluctuations in the plasma field or to variable random masking of the target surface from the applied plasma by the extrinsic species. This process is referred to herein as dynamic masking, as opposed to the static masking processes known in the field. Effects similar to those causes by extrinsic species may also be caused by the presence of impurities within the target surface to be etched. Irregular etching due to the presence of impurities is also considered to be encompassed by the term dynamic masking.

DETAILED DESCRIPTION OF THE INVENTION

In the present invention, the intensity and quality of the plasma to which a target material is exposed varies over time and space, producing a randomized, irregularly etched surface that is characterized by dimensional (i.e., depth and width) and morphological (i.e., geometry and porosity density) variations on the surface, having relief depths preferably at least 1 $\mu$m to about 20 $\mu$m, surface cavity diameters from about 1 $\mu$m to about 3 $\mu$m, and porosity densities in the range of approximately 4 to 120 pores per $\mu m^2$. In order to establish this plasma, low background pressures and relatively low power-to-surface-area levels are employed. Further, the inventive method plasma etching process is characterized by a dynamic masking, promoted by the presence of extrinsic species (e.g., water vapor, carbon dioxide, hydrocarbons, particulates, etc.), that are expected to be found in the reactor chamber environment at the relatively low pressures used (e.g., from $10^{-4}$ Torr to less than about 10 Torr).

In preferred embodiments, the present invention uses a radio frequency (RF) generated plasma, however, cold plasmas may also be generated by alternative methods (e.g., microwaves or direct current). The preferred low pressure cold plasmas of the invention are generated with radio frequencies of between 10 kHz and 27 MHz, most preferably, at 13.56 MHz; at pressures from approximately 0.01 to 0.20 Torr, with gas flows ranging from approximately 10 to 200 standard cubic centimeters per min (sccm), with gas temperatures typically between 300° and 600° Kelvin, with ion energies (potential) in an approximate range of 10 and 500 electron volts (eV), and approximate RF power densities between 0.05 and 1 watts (W) per $cm^2$.

In most embodiments, a noble gas is used to cool and stabilize the plasma and a reactive gas is used to effect the actual chemical etching process. In many embodiments, argon or helium are the preferred inert, noble gases. Reactive gases are used to create chemical species that will react with the target surface; the type of reactive gas is dependent on the material to be etched. The appropriate selection of the reactive gas requires that volatile reaction products be created in the reaction between the reactive gas plasma species and the target material, creating species that may be redeposited onto the surface and/or be carried away from the surface via the reaction chamber vacuum system.

Useful reactive gases used to etch a material may be selected from the repertoire of those well versed in the art of cold plasma, dry etching processes. In particular, those combinations of plasma gases that have been used in the semiconductor industry for regular etching and/or cleaning of circuit boards and electronic components. Suitable guidance can be found in the *Handbook of Plasma Processing Technology* (Rossnagel, Stephen M., Cuomo, Jerome J., Westwood, William D., (editors); Noyes Publications, Westwood, N.J., 1090) and *Cold Plasmas in Materials Fabrication* (Grill, Alfred; IEEE Press, Piscataway, N.J.; 1993), herein incorporated by reference. Generally, candidate volatile reaction products of the specific material surface will be identified, and reactive gases used in the RF plasma will be selected based on their potential to form the volatile species.

In those cases where suitable matches between plasma gases and the substrate material are not known, use of the present invention requires etching feasibility studies. Testing should be conducted in such a manner as to be able to determine the volatility of the plasma reaction products, their redeposition characteristics, the type of surface morphology changes, and the parameters of the plasma system used to bring about the etching reaction. The following steps are suggested when performing feasibility tests:

1) Chemically identify the material to be etched;
2) Determine the vapor pressures of candidate volatile reaction products capable of being generated from the material being etched;
3) Devise reaction scenarios that will generate the volatile reaction products; and
4) Identify reactive plasma gases capable of producing these reaction products by interactions with the target material.
5) Establish a reactive etching system, using the selected reactive plasma gases and comprised of a suitable reaction chamber, radio frequencies appropriate and RF power levels, power levels, vacuum levels, flow rates and concentrations, and etching times.

In addition to the reactive and inert gases used in the plasma, in some preferred embodiments, hydrogen gas is added to remove oxygen atoms from a target surface, or to retard the etch rate. In still other preferred embodiments, oxygen is introduced into the plasma to accelerate etch rates. In some embodiments, $O_2$ is used to oxidize harmful etching reaction by-products into a volatile species or also can be used to remove unwanted residual organic species by of the technique known as plasma ashing.

As an example of an etching system that is based on available plasma gas information, titanium can be etched with numerous combinations of halide gases (e.g., $BCl_3$, HCl, $CF_4$, $NF_3$, and/or $SF_6$) in a noble gas, such as helium or argon. In some processes, oxygen can be added to the plasma gases to increase the reactivity of the halide species with the titanium, while other scenarios will add hydrogen to the plasma to reduce the concentration of the free halogen radicals by combining with hydrogen atoms (e.g., $H_2+2\{F.\} \rightarrow 2HF$) which in turn can slow down the etching process. Noble gases act to stabilize, cool and dilute the reactive gases in the plasma, while halogen-based gases create the chemically reactive etching species. In some embodiments, inert gases, such as argon or helium, act as carrier gases when bubbled through liquid reactants, thereby increasing the evaporation rate of the liquid reactant into its vapor state.

Example 1 illustrates the use of a specific combination of gases for treating titanium. In this example, the argon provides some sputtering action on the titanium surface that re-deposits back to the surface as titanium filaments, but the $BCl_3$ is the primary reactant that chemically etches away the pure titanium metal surface, creating deeper etches than could be generated by noble gas plasmas alone. $BCl_3$ also introduces free chlorine radicals (Cl—) into the etching process that also react with the titanium surface. This etching action creates enhanced surface morphologies that make the inventive method useful for other applications.

In the case of surface treating a polymer, water vapor constitutes the reactive gas and argon the plasma stabilizing/cooling gas. Specific operating details for etching poly(L-lactic acid) (PLLA) can be found in Example 2. Water molecules are dissociated in the plasma to form activated moieties, such as OH— and H— radicals and/or other charged species. These species break polymer bonds and/or react with the organic components of the polymeric surface to create a more roughened and porous morphology.

As previously stated, the semiconductor industry routinely employs plasma technology for dry etching processes. Etching is used in the manufacture of circuit boards, silicon wafers and semiconductor devices. The etched surface morphologies or relief patterns, can be characterized by the relative amplitude or depth of the etch; that is, the depth of the etch with respect to the surface tangential plane at the point of the depth measurement. The specifically designed etch patterns for the electrical connections are carefully controlled through use of static masking techniques, the cleanliness of the etching environment, and the plasma operating parameters. Etching processes used in the semiconductor industry require etches that yield essentially smooth planar surfaces and/or circuit etch patterns of uniform depth. Generally, circuit pattern etch depths range from approximately one micron upwards to about fifteen microns. It is important to note that etched surfaces are intended to be as smooth as possible with no planar variations for optimum conditions, but typically having planar defects (or relief amplitudes) of less than 100 nanometers. Thus, the semiconductor industry surface relief amplitudes consequently have surface etch depths at least an order of magnitude less than those desired for medical implant surfaces.

The present invention utilizes cold plasmas to etch and modify the surfaces of metallic and polymeric medical implant devices, resulting in etched surfaces with irregularly distributed planar defects greater than 100 nm and preferably in the range of 1 to 20 $\mu$m. In preferred embodiments, the inventive method will yield shallow and/or deep irregular, random etch depths which will be between slightly less than 1 $\mu$m to 5 $\mu$m and greater than 5 $\mu$m to 20 $\mu$m, respectively, as measured from a surface's tangential plane at a specified surface location to the deepest point of the etch. Actual morphologies and surface etch depths are contingent upon the type of RF plasma gases used, the plasma operating parameters and the implant substrate material.

For metallic substrates, such as titanium, the surface morphology created by the inventive method appears to be comprised of filamentous elements. The filaments are defined as an elongated feature extending outward from the surface and having round, flattened or ribbon-like appearance. Filament of filamentous is used here as a descriptive term only and makes no inference as to the mechanism of morphology development or production. The individual filaments may be free standing, fused, or otherwise agglomerated in the final titanium surface modification. Fused or agglomerated filamentous substructures provide the appropriate morphology of the surface for implant devices. The increased microporosity and roughened surface that characterize this filamentous morphology correspond to an increased device surface area; thereby providing a more suitable adhesion surface for the application of chemically bioactive coatings (e.g., hydroxyapatite) or improved physical interaction with host tissue to secure a medical implant and/or promote cellular ingrowth. The preferred size for metal surface micro-protrusions will have approximate lengths of slightly less than 1 $\mu$m and up to 20 $\mu$m. Further guidance regarding etching of titanium surfaces can be found in copending U.S. patent application Ser. No. 08/786,869; herein incorporated by reference.

Polymeric materials also can be etched via the inventive method. Etched polymeric surface morphologies are similar to those produced with metals but appear to have a more fibrous, woven morphology. This surface configuration also provides a favorable surface for the promotion of cellular ingrowth or improved bioactive coating adhesion. In preferred embodiments, the depths of the woven or fused head-cilia patterns etched onto the polymer surface range from slightly less than 1 $\mu$m and up to 15 $\mu$m, with separation distances between the micro-strands ranging from 0.2 $\mu$m to 5 $\mu$m.

Figure 1:
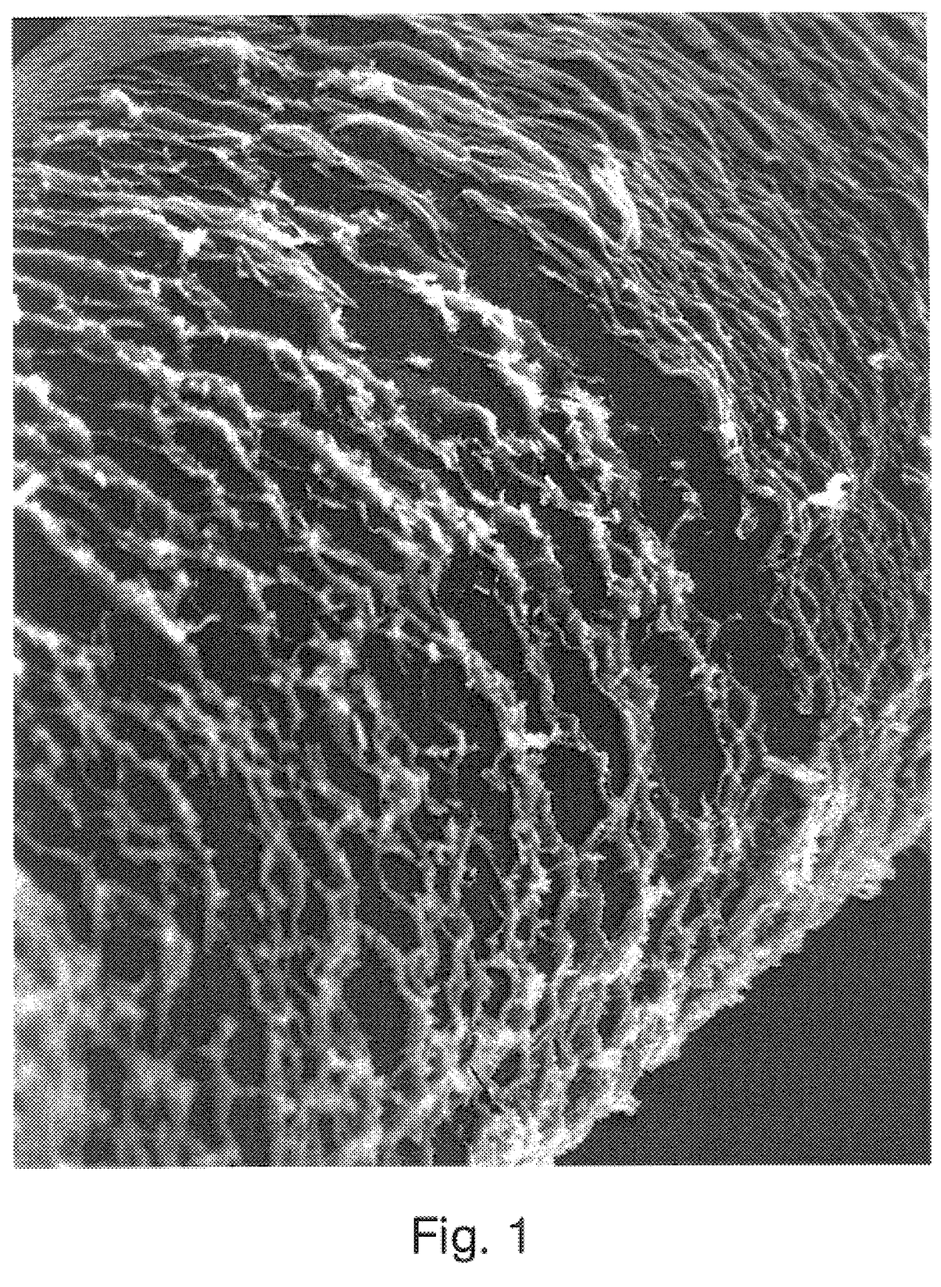
FIG. 1 is a photomicrograph of a nylon surface which has been plasma-treated according to the method of the invention to produce an irregular surface.
Figure 2:
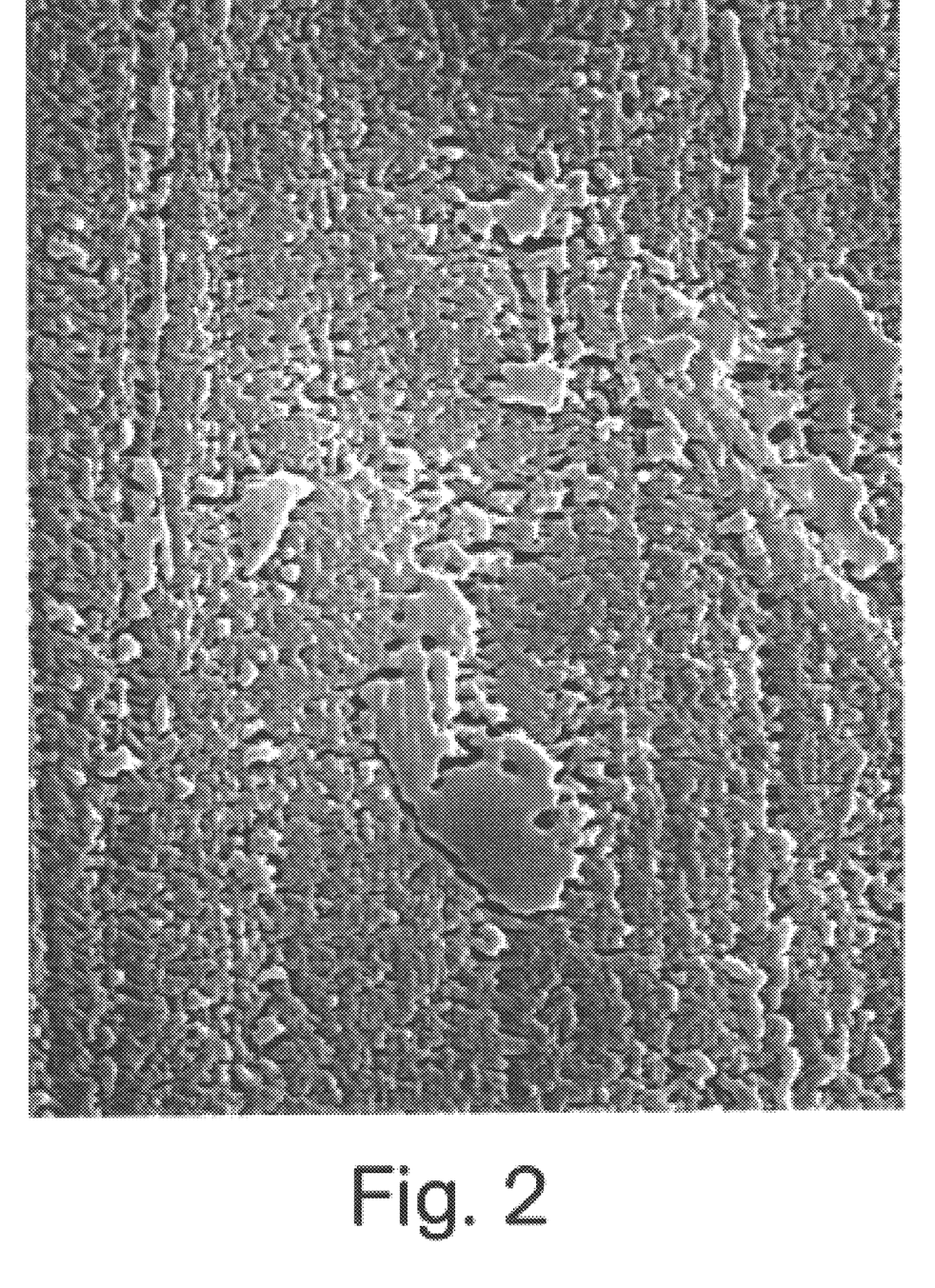
FIG. 2 is a photomicrograph of a poly(L-lactic acid) surface which has been plasma-treated according to the method of the invention to produce an irregular surface.
Figure 3:
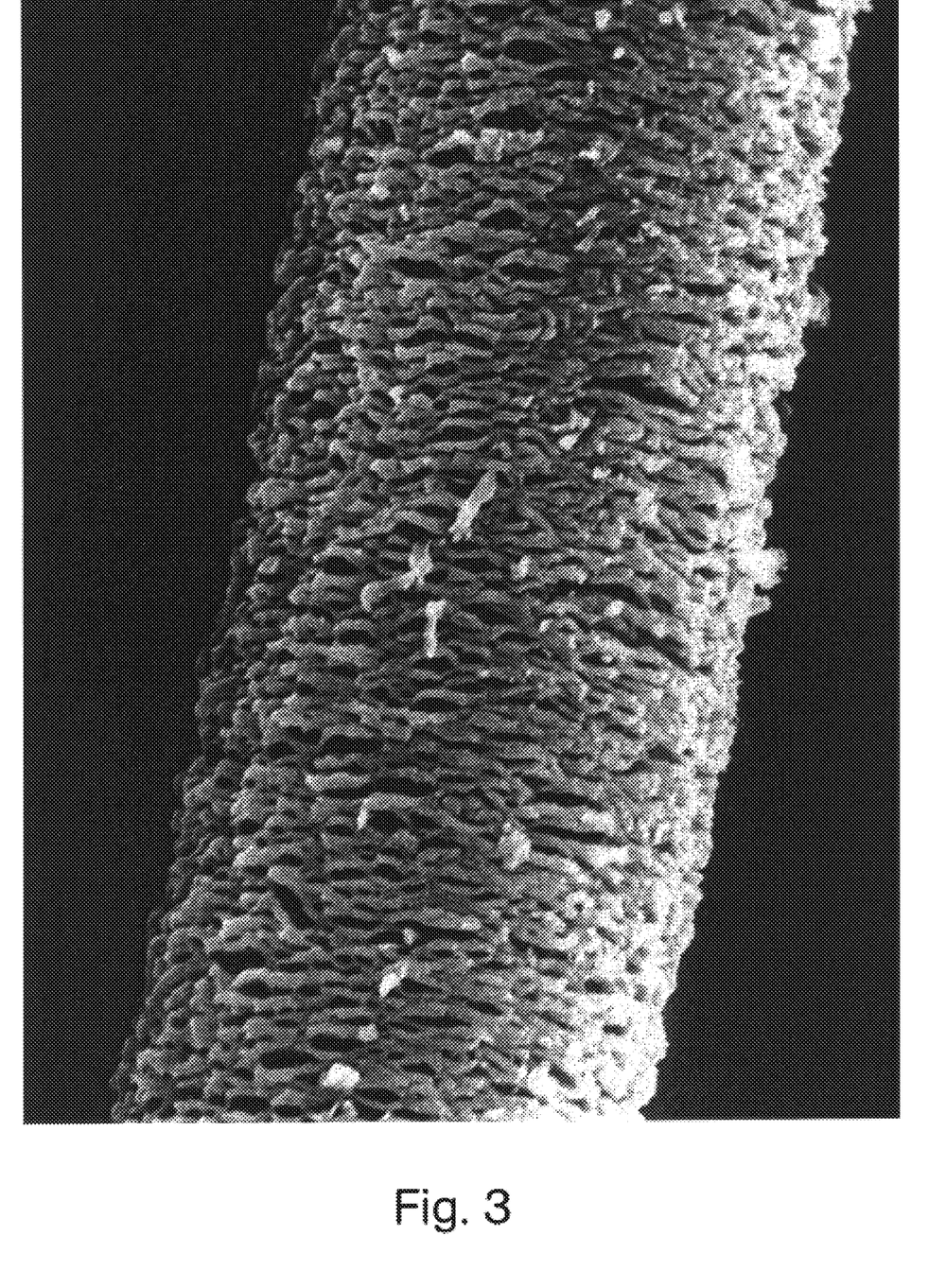
FIG. 3 is a photomicrograph of a poly(L-lactic acid) surface which has been plasma-treated in the presence of a sputtering agent according to the method of the invention to produce an irregular surface.

FIGS. 1, 2 and 3 show examples of polymeric surface morphologies produced by the invention. FIG. 1 shows the results of the inventive method etching of nylon. The remaining two figures present the results of two variations of the present invention's etching procedures for poly(L-lactic acid) [PLLA]: FIG. 2 shows the results of the etching process for a piece of PLLA with only the plasma, while FIG. 3 shows the resulting surface of a piece of PLLA with the introduction of a calcium phosphate as part of the dynamic masking process.

The invention utilizes specific etching parameters to create a desired surface topology. The inventive method's operational parameters depend on the target material's reactivity with selected plasma gases, along with the target item's size, density, surface area and plasma-accessibility to recessed and inner surfaces.

In preferred embodiments, the present invention utilizes non-local thermodynamic equilibrium (non-LTE) plasmas, or cold plasmas. Cold plasmas exhibit high electron temperatures of $10^{-4}-10^{5\circ}$ K. (1–10 eV), while the plasma gas can be as high a 300° C. or as low as room temperature. Because of their nonequilibrium properties, cold plasmas have the ability to bring about physical and chemical reactions with most gases at low temperatures. This property is particularly advantageous for materials that are thermally unstable, such as many polymers, but cold plasmas also may be used on higher melting point materials to achieve similar surface modifications.

The rate of reaction between the reactive gas and the target material affects the etch rate and the amount of time required to produce and etch depths of greater than 300–500 nm. The semiconductor art provides guidance on reaction rates of many known reactive gas/target material combinations. In the circumstances where guidance is required in determining etch time and/or reaction rate, an initial etch of 5–30 minutes may be tried. The target may then be examined for degree of etching by microscopy, such as scanning electron microscopy. Alternatively, the weight of target after etching may be compared to the pre-etching weight. Following this initial assessment, etching rate can typically be altered by changing reactive gas concentration or power levels. Increased relative concentrations of the reactive gas with in the plasma leads to faster etching rates and deeper etches in a shorter process time. Conversely, lower reactive gas relative concentrations produce slower etching rates. With no reactive gas, that is all the plasma is made up of the inert gas, the reactive ion etching mechanisms stop and surface modifications will occur as a result of plasma sputtering effects.

The operating parameters of the RF generator are selected to provide a plasma with the following features. In preferred embodiments, the usual RF is 13.56 MHz. In other embodiments of the invention, higher harmonics of 27.12 MHz or 40.68 MHz can be used to generate a plasma. In general, higher radio frequencies, up to 100 MHz, will increase ion bombardment activity and favor production of more dynamic masking activity, but lower radio frequencies are typically used maintain a more uniform plasma. The inventive method also can incorporate modulated radio frequencies. Radio frequencies are typically changed by using other RF generators specifically designed for alternate frequencies. As previously stated, changes in frequencies can result in plasma property changes, such as changes in ionic species charge densities, that will modify the surface in ways that are slightly different than a traditional RF plasma.

In preferred embodiments of the invention, RF power can be between 25 and 1000 watts (W). More preferable embodiments of the invention use wattages ranging from 75 W to 250 W. In still other embodiments of the present invention, modulation of the RF power level can be employed to modify the etching characteristics. Manual and/or programmed rapid and/or slow changes in the amount of radio frequency energy being supplied to the plasma are made as described in Example 4. In general, the RF power is set at an initial level, say 100 watts, and subsequently increased and decreased, say 25%, from the original power setting, at specified intervals, over the course of the etching period. Variations in power will effect the plasma's ability to etch a surface and can increase or decrease its ability to micro-sculpt the surface.

In some preferred embodiments, the inventive method can incorporate phase shifting of the radio frequency used to generate the plasma. Phase shifting the RF can cause the plasma to etch in ways that are different than conventional, unchanged radio frequency phase plasma etching processes. Manual and/or programmed, rapid and/or slow, or large and/or small changes of the RF phase are used to create additional surface modification effects. These phase shifts can change the impact and reactivity of the etching species, depending on the type of plasma gases used in the process. Consequently, a variation in the morphology can occur that is different from the more conventional uses of the inventive method.

In preferred embodiments, the size, shape, positioning in the reaction chamber, positioning in the plasma, and electrical connections (i.e., bias voltage) of the sample to be etched will effect the etching process and ultimately the surface morphology. Apparatus design and operating condition variables that effect the etching process can include the size of the reaction chamber, the volume of gases introduced into the chamber, the RF generator and power available, target cooling requirements and the plasma attributes. Those well versed in plasma dry etching techniques will be able to rely on their knowledge of the art to accommodate sample configuration tactics with respect to the aforementioned logistical examples. In a preferred embodiment, polymeric or metallic samples are placed in the center of the plasma and, in still other embodiments, are electrically connected to a RF generator or a DC bias is applied.

The inventive method can incorporate heating of the sample. Heating methods can include the following: constant temperature heating; ramped (incrementally stepped) increases of temperature heating; or gradual increased temperature heating. In terms of the reactive etching mechanism, heating lowers the activation energy required for the plasma. Thus, heating the sample surface increases the etching rate, thereby producing a deeper, more random roughening of the surface.

The inventive method can incorporate cooling of the target device that is to be etched. In a preferred embodiment, cooling devices, such as liquid nitrogen cold fingers, solid state cooler probes, or refrigeration coils, are attached to the target device so as not to hinder the plasma etching action. Cooling procedures can be varied and may include constant temperature cooling; ramped (incrementally stepped) decreases of temperature cooling; or gradual decreased temperature cooling. Cooling the device surface effects the kinetics of the plasma particles and tends to slow the etching rate leading to a more benign surface roughness that be required for a specific application such as plasma polymerization of an amine onto the surface of tantalum to facilitate attachment of amino acids. In preferred embodiments, when the sample articles are subject to melting at or near the operating temperatures of the process, some form of sample cooling is necessary.

An ultrasonic transducer can be attached to the target, allowing the transmission of ultrasonic waves directly into the device to provide in situ sonification. The resulting ultra-fast physical vibrations occurring at the surface can create different morphologies when compared to heating, cooling, and/or bias changes. The exact mechanics of this procedure are not fully understood. It is speculated that the minute vibrations of the device causes a change in the plasma species density at the surface, thereby etching the device with alternating high and low etching rates. The change in the etching rate alters the redeposition rate of the material onto the surface, which also causes the morphology to change.

The invention is not limited to a single, initial etching of an implant substrate. It is the intent of the invention to be used for any medical implant device surface, either applied to base substrate surfaces or any subsequent inventive method treated surfaces (i.e., coated, previously etched, or grafted), or multiple and/or successive surface conditioning steps in a manufacturing process.

Generally the surface to be etched will be fabricated from metals, polymers, ceramics or combination of these materials. The desired surface morphology created by the etching process should be appropriate for its intended use (e.g., to improve adhesive qualities for the application of coatings or improve tissue interactions). Plasma parameters must be matched to the material to be etched to produce appropriate volatile species.

The inventive method surface morphology changes are brought about primarily by the chemical interactions between the surface atoms/molecules and the excited plasma species that produce reaction products that are easily removed from the target surface (i.e., volatilized in a vacuum). Of less significance, there may also be some physical bombardment of the of the surface as a result of plasma particles striking the outer atomic and/or molecular layer which causes molecules to eject, or sputter, from the surface. This sputtering effect, although not the primary etching mechanism, is also embodied with the present invention. Sputtering also is another useful embodiment in the removal of an unreactive top monolayer, such as the typical oxide layers found on most metal surfaces. Further, some reaction products may be re-deposited back onto the surface, forming a different physical configuration which may contribute to the dynamic masking process, while others are swept away with the exhaust plasma gases.

When exposed to an inert gas plasma mixed with reactive gases, the target material surface will be modified primarily by chemical reactions that occur between the surface molecules and the excited ions or free radicals of the reactive gas. By using the right combination and concentration of the inert gas and reactive gas in the plasma, along with an appropriate target material, reaction products can be generated with vapor pressures that are sufficiently low enough such that they will be removed as a vapor from reaction chamber by way of the vacuum system without re-depositing onto the target surface. Chemical etching mechanisms are necessary when removing oxide or other potential masking compounds from metallic target surfaces. Masks are removed from the target surface to allow sputter etching, reactive ion etching and redeposition. Masking effects are of less importance for ceramic and polymeric surfaces, however they can cause problems when trying to achieve a desired surface morphology. Additional information regarding the masking-effect phenomenon is given in the co-pending U.S. patent application Ser. No. 08/786,869; herein incorporated by reference.

Titanium metal and a number of titanium alloys also can be surface treated by the inventive method. Metals that can meld with titanium to form titanium alloys include the following: aluminum, molybdenum, manganese, iron, vanadium, and zirconium (Zircaloys); alloys from these metal/titanium combinations are suitable targets for the inventive method. Noble gases and halide gases can be used to modify titanium and its alloys surface morphologies. Some suitable reactive plasma gases for some of the titanium alloys include $Cl_2$, $BCl_3$, and other halide containing gases that form easily vaporized compounds. Plasma etching creates reaction products that are volatile species (i.e., they have vapor pressures that are greater than the pressure of the reaction chamber, at the surface temperature) and are removed from the system; $TiCl_4$ is one such volatile species with a vapor pressure of approximately 10 mm Hg at room temperature. In preferred embodiments, the chamber is at a vacuum of approximately between 0.005 Torr and 1 Torr at approximately room temperature and typical surface temperatures of the target item within about 25° C. and 100° C.

Precious metals can be treated with the inventive method to obtain similar etching results and surface morphologies as with titanium or other metals. Precious metals include gold, platinum, silver, palladium, and their alloys. In a preferred embodiment, a suitable plasma used to etch gold contains $CCl_2F_2$ and Ar, as a stabilizer and coolant, with a flow rate in the range of 10 sccm to 90 sccm in a pressure range between 0.03 Torr and 0.1 Torr at an RF power level between 100 watts and 500 watts.

Ferrous alloys also can be etched by the inventive method; ferrous alloy substrates include Alnico (Al, Ni, and Co with Cu and/or Ti additives), stainless steels, carbon steels, chrome steels, cobalt steels, tungsten steels, Hastelloy, and Haynes Stellite 25 Alloy. Use of this latter alloy, Haynes Stellite 25, as an implant device has been described in U.S. Pat. No. 5,084,151 and here incorporated by reference.

Another metal substrate that can be etched by the inventive method is tantalum. Tantalum (Ta) is a heavy, gray and very hard metal that, when pure, is ductile enough so that it can be drawn into fine wire. The metal is completely immune to body fluids and has no reported irritating effects in the body, which is why tantalum is of interest and is thought to be an excellent substrate material for fabricating medical implants. In some embodiments, tantalum can be etched by plasmas composed of $CF_4/O_2$, $SF_6/O_2$, or $NF_3/H_2$ with operating conditions as given in Example 2.

Other metals and metal-like materials that can be etched with the inventive method include aluminum, boron, carbon, graphite, and tungsten. Examples of preferred plasma etching gases used with aluminum include chlorine-containing gases such as $CCl_4$, $BCl_3$, $SiCl_4$, and $CHCl_3$ and brominated gases such as HBr, $Br_2$, and $BBr_3$. Aluminum etches easily with these gases because the $AlCl_3$ is highly volatile at room temperature. $AlBr_3$ also is volatile, but at temperatures about 90° C. in the vacuum ranges used for the instant invention plasma which would require some additional heating of the Al target.

The present invention also is applicable to devices fabricated from polymeric materials, thereby preparing the polymer surface for subsequent coating of metals, or other chemical compounds, biological components, laminates, and/or polymer coatings. These coatings can be further etched by the RF plasma with the appropriate operating parameters, further altering the surface. A wide array of potential polymeric materials useful in biomedical applications exists. Descriptions and references can be found in *Principles of Tissue Engineering* (Lanza, R. P., Langer, R, and Chick, W. L.; Academic Press, Austin, 1996) and *Cold Plasma in Materials Fabrication* (Grill, Alfred; IEEE Press, Princeton, N.J., 1994); herein incorporated by reference. Dynamic masking for polymers is provided through the use of low vacuums (>0.1 torr) and/or sputtering process to provide exogenus species.

A three-step mechanism of the clean etching of polymers has been described by Hartney el. aL (*J. Vac. Sci Technology.*, B7: 1 (1989)), incorporated herein by reference. By clean etching, as that term is used herein, it is meant an etching process which seeks to produce clean and regular etched surfaces without the surface roughness of the instant invention. Such processes are typically conducted under high vacuum, e.g., less than 0.01 torr and in the absence of minimal target material impurities, sputtered ions or other materials or processes which contribute to the dynamic masking process. First, when using $O_2$ in the plasma, the oxygen atoms remove hydrogen atoms from the polymer and fragment the surface, leaving activated species on the surface. Second, further reactions between molecular oxygen and the now activated surface species form precursor volatile reaction products. Finally, in the third step, plasma ion bombardment removes the volatile moieties that are subsequently carried away from the surface and ultimately removed from the reaction chamber via the vacuum system, thereby completing the etching process. Generally, the etching of most polymers can be done with either $O_2$, $O_2/CF_4$, or water vapor as the reactive gas. In other embodiments, chlorine-containing gases, $H_2$, $Ar+O_2$, $SF_6+O_2$, and $H_2O$ are used to etch polymers. The latter compound, water, in combination with argon was used to etch the polymer poly(L-lactic acid), as described in Example 3. Dynamic masking was implemented by the vacuum conditions used.

The following identifies some of the polymers that can be used with the present invention and in the fabrication of medical implant devices. New polymers are routinely being invented and introduced for commercial use. Therefore, the polymers cited below do not necessarily constitute all possible uses of the inventive method with all current or future polymers, and are given as broad examples.

Poly(L-lactid acid) [PLLA], poly(glycolic acid) [PLGA], and poly (lactide-co-glycolide)[PLGA] PLLA, PGA, and PLGA are biodegradable polymers that can be etched with a noble gas RF plasma and water vapor at temperatures from about 25° C. to about 50° C. with chamber pressures preferably between about 0.1 Torr and about 1 Torr. When etching these polymeric materials, RF power levels should be between about 10 and about 200 watts; preferably between about 50 and about 150 watts. Some of the workable plasmas used to etch these polymers include helium or argon with reactive gases such as water vapor, oxygen or hydrogen. Other embodiments of the reactive gas plasma can include halogenated hydrocarbons, such as carbon tetrachloride, perchlorofluorocarbons (freons) or chloroform; or inorganic halide gases, such as fluorine or chlorine. The invention is capable of creating a micro-porous, fibrous surface that can be readily coated with an appropriate bioactive material (see FIGS. 1, 2 and 3).

Polyethylene [PE] is a suitable polymer for etching via the inventive method. In preferred embodiments, conditions for etching the surface of high-density polyethylene (HDPE) require the use of either a He plasma, a $F_2$/He plasma or a $CF_4$/He plasma with an operating temperatures between 25° C. and 100° C. and pressures in the range of 0.005 to 0.20 Torr. RF power levels should be between about 10 and about 200 watts.

In another preferred embodiment of the inventive method, the surface of iso-polypropylene [PP] can be etched with a RF plasma made up of He, $F_2$/He or $CF_4$/He gas combinations, at an operating temperature between 25° C. and 100° C. and pressures in the range of 0.005 to 0.20 Torr. RF power levels should be between about 10 and about 200 watts.

In a specific embodiment of the inventive method, Polyurethane [PEU] also can been etched using a plasma comprised of a noble gas mixed water vapor at low pressures (0.005–0.20 Torr) and near room temperatures (20–30° C.). RF power levels should be between about 10 and about 200 watts.

Other polymeric materials that are used, or potentially can be used, for implant devices include the following: Polysulphone [PSu], Poly(tetrafluoroethtylete) [PTFE] (e.g., GORTEX®), Poly(methyl methacrylate) [pMMA], Poly(2-hydroxyethylmethacrylate) [pHEMA], Polyacrylonitrile [PAN], Polyamides, Poly(vinzyl chloride) [PVC], Poly (ethylene-co-vinyl acetate), Polystyrene [PS], Poly(vinyl pyrrolidone) [PVP], Poly(acrylonitrile)/Poly(vinyl chloride) [P(AN/VC], Polyacetal Resins (e.g, medical grade DELRIN®) and/or Polyester Resins (e.g., medical grade DACRON™—polyethylene terephthalate).

Ceramics are not typically etched because of their hardness and brittle characteristics, as well as their chemical nature as homogeneous oxides. Some ceramic materials are capable of being chemically etched with plasmas composed of the appropriate reactive gas, such as oxygen and fluorine, but do not undergo redeposition as with metals.

Surfaces that have been previously modified by the present invention can be further modified to improve their performance for specific uses. Mechanical techniques such as traditional machining (i.e., scoring, drilling, brushing, etc.) and/or milling can be used to further alter the inventive surface. In some embodiments, metallic powders (large and/or small grain sizes) can be plasma sprayed onto a previously etched surface giving it a macro-abrasive morphology. Once a secondary treatment has been applied to surface, the inventive method can be used again to further modify the surface configuration.

Additional surface treatment processes may be applied to devices previously conditioned by the invention. These optional, post-etch procedures may include, but are not limited to some, or combination, of the following commonly used surface coating/treatment methods: wet or dry coating applications, plating, vapor deposition, anodizing, surface polymerization, and re-etching of previously coated and/or etched surfaces of a device. Post-etch operations can be employed to either prepare the surface for a desired morphology or to make the surface smooth without any configurations.

Immobilized artificial coatings can be applied to medical devices to enhance biocompatibility. In many cases, these coatings do not satisfactorily adhere to the implant substrate surface. Existing techniques used in preparing immobilized artificial bioactive coatings are problematic, in that once applied, coatings often become mobile and loosen from the implant surface. Further, inadequate coating processes do not provide sufficiently dense, uniform coverage of the desired biomaterials or gaps that can occur on the implant surface where the coatings did not properly adhere to the substrate. Some of the current implant device surface coating techniques include plasma grafting, plasma polymerization, dip coating and sputter coating.

As previously stated, the inventive method enhances medical implant surfaces by improving the adhesion characteristics of the substrate, which in turn provides for better coating uniformity and thickness of biocompatible polymeric materials because the invention roughens and changes the micro-morphological configurations of the surface. Some of the immobilized polymeric coatings that can be used include: polyolefins, polyamides, polyimides, polyethers, polyesters, polystyrenes, polyvinyl chlorides, polypropylenes, polyisoprenes, polytetrafluoroethylenes, polyurethanes, polycarbonates, polyalkylimines (in combination with cross-linking agents: glutaraldehyde, glyoxal, malonaldehyde, succinaldehyde, adipaldehyde, or dialdehyde starch). U.S. Pat. No. 5,415,938 and U.S. Pat. No. 5,415,938, herein incorporated by reference, identify some of the existing art used to polymer coat medical implant devices.

Pyrolitic carbon material, excluding graphite, has been deposited on a variety of device substrates, including medical implants, via vacuum-vapor-sputtering using ion-beam generated carbon aerosols. It is possible for the surface of these carbon coatings to be further etched via the inventive method, and subsequently coated. A description of one of these processes can be found in U.S. Pat. No. 5,084,151; incorporated herein by reference.

Application of silicon-containing materials (organic and/ or inorganic compounds) is contemplated by this invention. Aminopropylsilanes can be coated onto silica surfaces, providing a stationary membrane when covalently bonded with acyl chains of phospholipids. This technique provides a sterically useful "spacer arms" between the silica surface and the phospholipid. Descriptions of some of these types of processes have been described by Markovich et al, (*Anal Chem.*, 63:185 (1991)) and also can be found in U.S. Pat.

No. 5,217,743; incorporated herein by reference. Si—H also has been polymerized onto the surfaces of silicone rubber and also can be seen in U.S. Pat. No. 5,364,662; incorporated herein by reference.

Implant device surfaces can be chemically modified after the invention has been applied. Chemical modifications can include surface polymerization via plasma reactions; polymer application via sprays, dipping, or cold vapor deposition; acid etching; electroplating; and/or passivication.

Chemical dipping techniques for metallic and polymeric materials are commonly used in the metal finishing and polymeric coating industries. These chemical dipping techniques also can be applied to medical implant devices where appropriate in their fabrication. The art of chemical dipping processes is known and suitable guidance can be found in *A Guide to Metal and Plastic Finishing* (Maroney, Marion L.; 1991), *Basic Metal Finishing* (Von Frauenhofer, J. A.; 1976), and *Surface Finishing Systems: Metal and Non-Metal Finishing Handbook-Guide* (Ruazki, George J.; 1984); and are incorporated herein by reference.

Conventional metal and polymer surface treatment processes such as chemical etching, passivation and electroplating can further modify the invention-treated medical implant device surface. Techniques for metallic and polymeric materials are commonly used in the metal finishing and polymeric coating industries. Further, these options may include one or combinations of the following: acid dipping, pickling, passivation, and electroplating of nickel, copper, chrome, titanium, precious metals and/or other commonly used plating metal and metallic compounds. A description of the art of surface conditioning by chemical etching, electroplating, and passivication is too extensive and cannot be included as part of this application, but suitable working knowledge of the art can be found in *Techniques in Electrochemistry, Corrosion, and Metal Finishing: A Handbook* (Kuhn, Anselm T.; 1988), *Electroplating Engineering Handbook* (Durney, Lawrence J. (editor); 1984), and *Practical Electroplating Handbook* (Parthasaradthy, N.; 1989); and ); and are incorporated herein by reference. In should be noted that the inventive method also can be applied successively to newly coated surfaces to further micro-sculpt and/or add other coatings and/or surface pretreatment processes.

The inventive method facilitates texture application and surface micro sculpting of surfaces such as medical implant device surfaces. Suitable textures can be applied which allow interlocking and/or anchoring of coatings and tissues. As previously mentioned, the present invention is particularly beneficial in anchoring bone growth stimulation (BGS) type coating materials (e.g., amorphous calcium phosphate, poorly crystalline hydroxy apatite [α-BSMt™], etc.) for application onto orthopedic prosthetics. Improved anchoring of the BGS coatings, as a result of the implant surface enhancements, is conducive to enhanced stability of bone in growth and interaction while exhibiting good biocompatibility properties with an implanted prosthetic. Similarly, the invention also can be used on a large number of other medical implant devices with a variety of biological and/or chemical species coatings. The following is a partial listing of additional uses of the invention with respect to invention-treated implant device surfaces.

The use of this invention with polymer medical implant devices can modify the surface allowing enhancing the ability to graft polymeric monomers or covalently couple other species onto the medical device surface that are more favorable to cell- and tissue-bonding. Some methods and references to other methods for the application of biocompatible surfaces are described in *Surface Modification of Polymers for Medical Applications*, Y. Ikada, Biomaterials (August 1994, 15 (10) p. 725–36); incorporated herein by reference. Some biological-based, biocompatible medical implant device coatings include the following: cell adherent surface-coatings, endothelial cells, functional groups, and/or growth enhancing factors/media. This latter category, cellular growth enhancing substances, may include some of the following materials: amine groups (potentially created and bonded to a surface with via RF $NH_3$ plasma), amino acids, carbohydrates, sugars, alcohols, chelating and/or ligand groups, enzymes, catalysts, hormones, lectins drugs, proteins, peptides, antibiotics, vitamins, antibodies, antigens, nucleic acids, and DNA and/or RNA segments. In general, these materials can be applied wet by dip coating or as gels and left wet or dried.

Applications of the Inventive Method with Medical Implant Devices

The object of the invention is to modify the surface of a medical implant to allow for optimized tissue interaction matched to the intended function of the implant, such as the production of surfaces either biological or chemical in nature and biocompatible; as a result of changed surface topology and/or texture. Materials used to manufacture medical implant devices can be molded, machined, cast or fabricated from knitted, woven or braided materials. Further, there are additional factors to consider when designing and fabricating implant devices. In particular, it must be ascertained whether biocompatible coatings will, or can, be applied in vitro or in vivo in that the way coatings are applied may be contingent on the functionality and type of device implanted.

For most medical and surgical procedures, the surface of polymeric implants must be both biocompatible and functional. RF plasma pretreatment of polymeric materials will condition the surface in such a way as to facilitate the appropriate substrate conditions to negate thrombogenic conditions, either through the addition of specific biocompatible coatings and/or the etching or smoothing process itself. This latter case is of importance when no texture is needed. Creation of a smooth surface where adhesion is not wanted because of the nature of the therapeutic procedure and its potential medical complications when cells attach is another embodiment of the present invention's preparative properties.

As an example, artificial blood vessels require low wall shear stress rates so that the blood flowing by the wall surface does not adhere to the wall and the appropriate wall surface topologies and chemical composition are present so that platelet adhesion to the surface is eliminated or minimized to the point at which there is no danger of forming thrombi. An initial use of the inventive method etching process creates enhanced adhesion surface characteristics that are necessary for applying bioactive coatings that can exhibit improved blood flow shear rate conditions and give rise to better anti-thrombogenic properties, when compared to the untreated substrate material.

In preferred embodiments of the inventive method, plasma etching can physically modify and enhance the substrate micro-surface morphology of an implant device, thereby providing a suitable cell anchorage morphology. For some materials however, in addition to the application of texture to the surface, a suitable conditioning also must be applied to promote cell attachment and/or growth and differentiation. Textured surfaces may be further conditioned for cell attachment through the application of growth matrix materials or components. Suitable conditioning materials include Matrigel, collagen, fibronectin, or laminin. In preferred embodiments, poly(L-lysine) or poly(L-ornithine) is applied through dip coating and drying. Following this conditioning step, cells are applied either in vitro or in situ. In the cases of cardiovascular implants such as shunts and valves, endothelial cells are the preferred cell types. Cells may be applied to the implants either as primary isolates or established cell lines.

The following presents a partial listing of some of the medical implant devices that could benefit from the use of the present invention. The examples of medical devices given below do not necessarily constitute all devices that could be benefit from the use of the inventive method.

Artificial Organs and Organ-Repair Implants

The invention can be applied to substrate material surfaces that are used in the preparation of scaffolds and/or matrices that are subsequently used to fabricate surgical implants for diseased or impaired organs or used to grow whole, artificial organs. Starting materials for these implants or artificial organs are generally biocompatibile, are often resorbed by the body, provide the appropriate structural integrity and support, and should be able to withstand the conditions of the invention. A variety of materials have been used in scaffold applications such as, but not limited to, tubular, fibrous, filamentous, and woven polymers, and natural materials. Other starting material configurations suitable for scaffold fabrication include woven or knitted items, micro- or nano-spheres (i.e., fullerenes), micro- or nano-tubes, cobweb-like configurations or foams/sponge-like forms. Any of these materials may be etched by the methods of the instant invention. Once the implant substrate material's surface is textured and its adhesion properties are enhanced, the appropriate cell growth materials and processes can be applied to the enhanced surfaces either in vitro or in situ.

Cardiovascular, Vascular and Associated Implant Devices

The application of appropriate surfaces to cardiovascular or vascular implants can be used to improve the biocompatibility of medical devices meant to be implanted into the body. In those cases where the implant's surface interfaces with blood, other body fluids and/or tissue, the inventive surface micro-sculpting techniques, coupled with post-etching chemical and/or biological coating of cardiovascular implants is useful to prevent formation of thrombi, aggregation and ultimately emboli. The following is a partial list of cardiovascular and vascular medical implant devices whose surfaces can be conditioned using the invention.

Blood Vessels and Vascular Grafts

In situations of coronary artery blockage as a result of arthrosclerosis, where the flow of blood to the cardiac muscles is reduced or blocked by plaque, coronary by-pass surgery is used to restore blood flow. A common procedure to remedy this dangerous situation is to remove a portion of a vein from the leg. The coronary arteries are by-passed by attaching the donated veins from the aorta to the coronary artery end attached to the heart, by-passing the clogged area of the vessel. Artificial vascular implants sometimes have been used instead of autografts but have not been as successful in maintaining the appropriate blood flow and/or non-thrombogenic properties as self-donated blood vessels. This situation is the result a number of factors, some of which include accelerated formation of plaque resulting from unnatural fluid dynamics of the blood and inner wall gaps and lack of continuous biocompatible coatings that establish sites which are susceptible to aggregation of platelets and other clotting materials. The present invention can be used to modify the inner and/or outer surfaces of artificial coronary arteries to enhance processes that result in more biocompatible functionality of the by-pass implant. Specifically, once the appropriate micro-sculpting (0.5 $\mu$m to 15 $\mu$m etch) has been achieved by the inventive method biocompatible coatings such as Teflon, polyurethane, or poly(acrylonitrile/vinyl chloride) [P(AN/VC)], a biocompatible copolymer, can be applied to create a smooth, highly stable coating that exhibits anti-thrombogenic properties. Alternatively, a post-etch application of a growth promoting interface such as collagen or poly-lysine can be added to promote highly efficient adhesion of endothelial cells with a reduced likelihood of migration or detachment.

In other situations where trauma to blood vessels or thrombosis has occurred, the flow of blood to and from other areas of the body is impaired. Vascular grafts are one method to repair the vessel. A common procedure for repairing these damaged blood vessels is to remove a portion of a vein from another area in the body and, after the damaged vessel is surgically removed, the "donor" blood vessel is grafted into the damaged vessel. As with by-pass procedures, synthetic vascular implants have not been as successful in maintaining the appropriate blood flow and/or non-thrombogenic properties. As described previously, the present invention would be used to initially condition the inner and/or outer surfaces of artificial blood vessels to enhance coating processes, resulting in enhanced biocompatibility and functionality of the vascular graft implant compared to existing artificial implants.

Heart Valves

Two approaches to repair or replacement of heart valves exist: (1) the use of tissue or (2) the use of mechanical devices and prosthesis. Tissue valves are more favorable than mechanical valves, but do not have the same durability, rarely lasting more than fifteen years after implant. Failure rates for non-autologous tissue valves are associated with calcific degeneration, a result of the implant's incompatibility with the body. Other complications can occur with both types of heart valves due to material and tissue culture limitations.

Tissue engineering can be employed to improve and augment existing heart valve repair and replacement technologies. Materials used to repair and fabricate heart valves can be enhanced for improved biocompatibility through surface conditioning via the invention and the appropriate bioactive coatings.

The preferred heart valve is a tissue prostheses because they are quiet, do not induce turbulent flow, do not require a lifelong therapy of anticoagulants and failure is a slow process rather than sudden as with mechanical valvular prostheses. Artificial mechanical valves tend to calcify more easily and initiate immune system responses as a result of their composition: metals, polymers or other synthetic materials. The use of the present invention to modify the surfaces of these materials to become more adhesive for biocompatible coatings and/or cells or tissues can minimize calcification complications when appropriately utilized.

Blood Oxygenators

Blood oxygenators are one example of the way the inventive method can be used to improve diffusion of gases across a membrane. Blood oxygenation implant devices are used to transfer oxygen to the blood stream without the use of the pulmonary system. They typically are fabricated with layers of polymeric membranes that permit gaseous oxygen molecules to diffuse into the blood stream while preventing blood serum and other components from passing out of the blood stream.

In preferred embodiments, the surfaces of polymeric membrane material can be modified with the inventive method to create morphologies that can enhance the membrane's ability to be coated with substances that increase the diffusion rate of gases across the membrane, thereby improving oxygen transport into blood. Suitable diffusion enhancing are known to practitioners of the art and include perfluorocarbons and oxygen storage-and-transport molecules.

Catheters

Surfaces of catheter-type devices also can be treated with the inventive process and subsequently coated with the appropriate biocompatible materials. Catheters having functional species mixed in with the biocompatible material coatings will reduce medical risks associated with the device and procedures, as well as their extended use, thereby reducing overall medical and nursing cost.

Balloon Angioplasty Catheters

A method to remove coronary artery blockage utilizes very thin catheter devices that are typically inserted through the femoral artery and guided into the site of the blocked coronary artery. Once in place, a balloon device is inserted through the in-place catheter and inflated inside the artery blockage to enlarge the artery's opening, thereby improving blood flow to the heart muscle. Some improvements to angioplasty catheters have been made, as described in U.S. Pat. No. 5,254,372 (Nichols, Oct. 19, 1993), but further work is needed to minimize immediate and post-procedural risks. The present invention can be used to condition the surface of the catheter portion of the device and the balloon so that they can be coated with biocompatible materials, such as anticoagulants and anti-inflammatory agents that would help lessen the risk of emboli or further artery wall damage.

Urinary Tract Catheters

Urinary tract catheters are inserted through the urethra into the bladder to ensure unrestricted urinary output in situations where patients are incapacitated as a result of trauma, disease or surgical procedures. These devices typically are kept in place for up to eight hours when using straight-line catheters or for several days to weeks with catheters equipped with balloons that are inflated in the bladder. Both types of catheter can cause urinary tract infections and tissue irritation. The use of this invention can create surface enhancements that enhance the stability of suitable biocompatible materials coatings, minimizing infection and/or other medical complications associated with the procedure.

Central Venous Catheters

These devices represent another category of catheters used for long-term intravenous delivery of antibiotics, blood, and chemotherapy agents. They are typically inserted through large veins in the neck or upper torso (e.g., jugular) and into the atrium of the heart. Currently, their long-term use can increase thrombogenic risks and cause irritation or infection at the insertion site, potentially threatening cardiac complications. The invention provides a means to prepare an internal and/or external surface enhancement so that a suitable surface for biocompatible material coating is created.

Shunts

This type of catheter is used in patients with renal disease requiring long-term dialysis treatment. Shunts are typically put into an arm or leg for easy connection to dialysis systems. Similar problems and risks occur with these devices as with central venous catheters. The invention may be used to enhance the inner and outer surfaces of these medical devices for application of biocompatible coatings, minimizing the threat of thombosis, vein irritation, or additional surgical procedures.

Intravenous (IV) Solution Delivery

IV delivery systems are a commonly used device that delivers IV solutions through a needle inserted into a vein on the back of a hand or further up the arm. The needles are meant to be in-place for a short time (i.e., less than four or five days), but still can cause tissue and vein irritation. Mid-line and long IV catheters are also used for delivery of IV solutions, with a maximum in-place-time of two weeks. They are inserted a minimum length of six inches into a large vein of the upper arm or leg. The invention can enhance inner and outer surfaces of the IV needles and catheters, preparing the surfaces for application of biocompatible coatings that would allow longer in-place periods and minimize medical complications and costs.

Electrodes

In neural, cardiac and some other procedures, the implantation of electrodes into living tissues is required to provide electrical stimulation to tissue. In such situations, the more biocompatible the implant device with surrounding tissues and blood vessels, the lower the risk (i.e., tissue rejection, infection, malfunction of the electronic portion of the pacemaker device, etc.) involved in the procedure. The instant invention may be used to enhance the attachment of biocompatible.

Implant Wire Insulation

The invention can be used to affix and apply biocompatible insulating materials (i.e., polymers) to sheath implanted electrodes and lead wires, thereby lowering the risk of medical complications (i.e., tissue rejection, infection, malfunction of the electronic portion of the pacemaker device, etc.). In preferred embodiments, the invention can be used to etch the surface and apply a suitable insulating, biocompatible coating onto the implant wire.

Other Medical Devices

The inventive method can be applied to sutures, surgical staples, and surgical grafts, meshes, screens, and patches where applicable and per appropriate medical procedure. Such surgical devices can be used for hernia and aortic aneurysms surgeries. Otological prostheses used in ear cases where the fine bone structure of the ear has been traumatized. Dental prostheses for reconstructive surgery and bone repair would also benefit from the use of the inventive method and subsequent coating processes.

EXAMPLE 1

Titanium

Titanium (Ti) is an excellent substrate material for fabricating medical implant devices. In particular, orthopedic and dental prosthetics are often made of titanium metal.

A small plate of commercially pure titanium metal was initially pre-cleaned with a series of sonications using various organic solvents and distilled water rinses, then oven dried, and placed in a plasma reaction chamber which was subsequently evacuated to $5\times10^{-5}$ Torr. An oxygen plasma was generated for 5 minutes to remove residual organic material that may have been in the chamber. $O_2$ plasma conditions were as follows: $O_2$ pressure at 0.02 Torr and a RF power level at 150 watts. Chamber temperature was kept at approximately 25° C. (room temperature) throughout the process.

Two stages of the reactive etch process were carried out in the following order: (1) an initial oxide breakthrough procedure was performed to remove the previous cleaning step's oxide formation on the metal target and (2) a reactive ion etching step.

The oxide breakthrough step used a mixture of $BCl_3$ at 20 standard cubic centimeters per minute (sccm), $Cl_2$ at 10 sccm and He at 30 sccm with a chamber pressure of 0.05 Torr. The RF was operated in the voltage mode with a sheath voltage between the plasma and metal target set at 300 volts; the RF power level initially was set at 200 watts. Breakthrough was allowed to occur for 30 seconds.

The mixing ratio of reactive gases was changed for the etching step: $BCl_3$ flow rate was decreased to 15 sccm, $Cl_2$ was increased to 10 sccm and He remained at 30 sccm. The chamber pressure was reset to 0.04 Torr. The RF power source was switched to the power mode and initially set to 100 watts with a sheath voltage setting of 250 volts. Reactive etching was carried out for a total of 60 minutes.

At the end of the etching period, the RF generator power was turned off and the chamber was evacuated to $5 \times 10^{-5}$ Torr. A final oxygen plasma cleaning step was performed to remove any residual surface hydrocarbon contamination. Conditions were as follows for this last step: $O_2$ pressure at 200 Torr, $O_2$ flow rate at 30 sccm, and a RF power level at 150 watts. The final $O_2$ cleaning continued for 15 minutes, at which point the plasma was turned off, the chamber was allowed to vent to standard atmospheric conditions and the etched item was cleaned by ultrasonic techniques.

Figure 4:
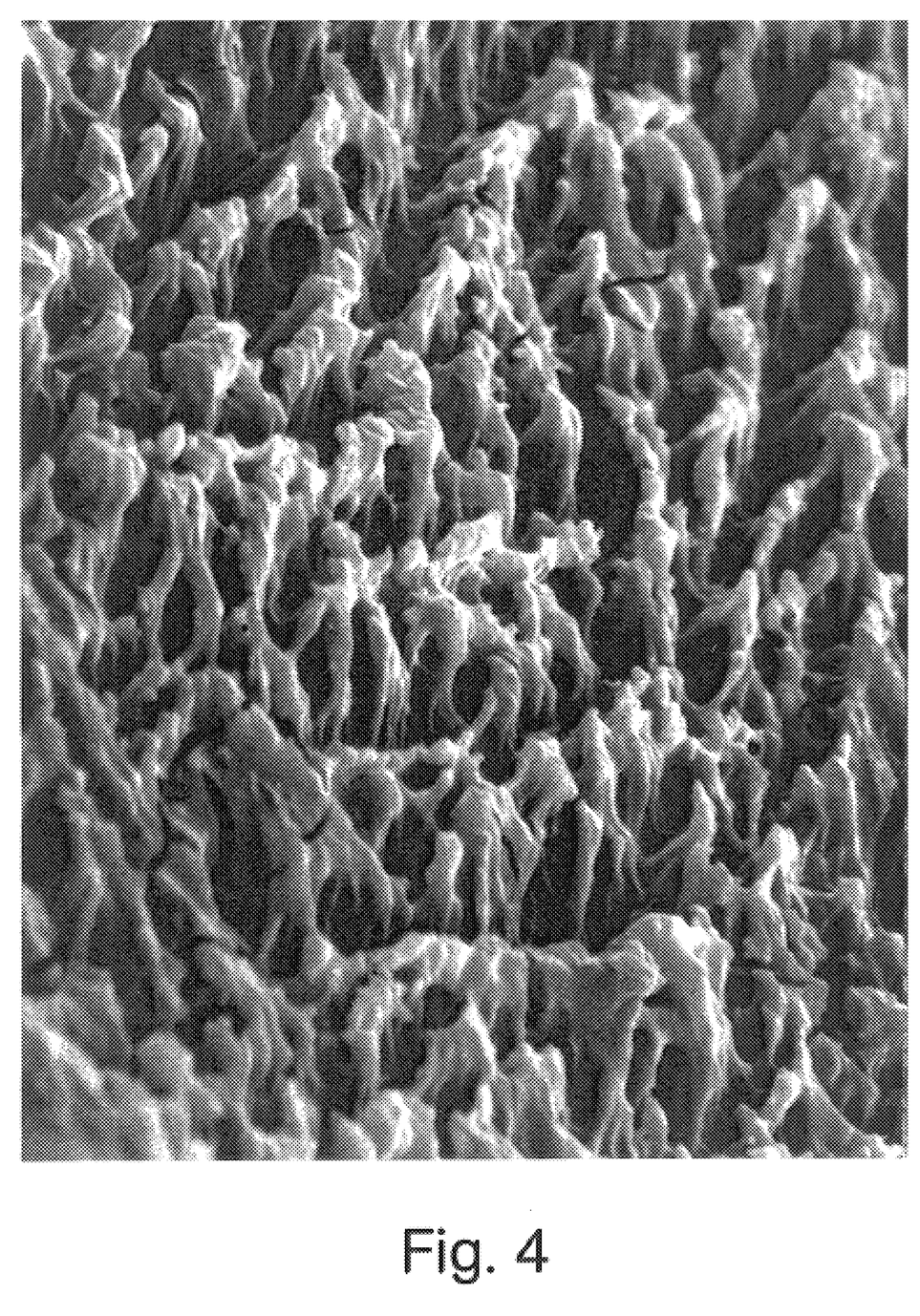
FIG. 4 is a scanning electron microscope (SEM) photograph of a titanium surface produced by the method of the invention.

FIG. 4 is a scanning electron microscope (SEM) photograph of the surface produced by this method.

EXAMPLE 2

Tantalum

A 4-cm length of Ta wire (0.10 mm diameter) is pre-cleaned with a series of sonications using various organic solvents and distilled water rinses, then oven dried, and placed in a plasma reaction chamber which is subsequently evacuated to $5 \times 10^{-5}$ Torr. An oxygen plasma is generated for 5 minutes to remove residual organic material that may have been in the chamber. $O_2$ plasma conditions are as follows: $O_2$ pressure at 200 Torr and a RF power level at 150 watts. Chamber temperature is kept at approximately 25° C. (room temperature) throughout the process.

An initial oxide breakthrough procedure is performed to remove the previous cleaning step's oxide formation on the metal target followed by a reactive ion etching step. The oxide breakthrough step uses a mixture of $CF_4$ at 20 standard cubic centimeters per minute (sccm), $F_2$ at 10 sccm and Ar at 30 sccm with a chamber pressure of 0.05 Torr. The RF generator is operated in the voltage mode with a sheath voltage between the plasma and metal target set at 300 V; the RF power level initially is set at 200 watts. Breakthrough is allowed to occur for 30 seconds.

The mixing ratio of reactive gases is changed for the etching step: $BCl_3$ flow rate is decreased to 15 sccm, $Cl_2$ is increased to 10 sccm and He remained at 30 sccm. The chamber pressure is dropped to 0.04 Torr. The RF power source is switched to the power mode and initially set to 100 W with a sheath voltage setting of 250 V. Reactive etching continues for a total of 60 minutes.

At the end of the etching period, the RF generator power is turned off and the chamber is evacuated to $5 \times 10^{-5}$ Torr. A final oxygen plasma cleaning step is performed to remove any residual surface hydrocarbon contamination. Conditions are as follows for this last step: $O_2$ pressure at 200 Torr, $O_2$ flow rate at 30 sccm, and a RF power level at 150 watts. The final $O_2$ cleaning continued for 15 minutes, at which point the plasma is turned off, the chamber is allowed to vent to standard atmospheric conditions and the etched item is cleaned by ultrasonic techniques.

EXAMPLE 3

Helium Vs Argon Plasma Etching of Poly(L-Lactic Acid)

For this example, poly(L-lactic acid) [PLLA] suture material (0.05 mm diameter) was subjected to a helium and an argon plasma with a small amount of water vapor. PLLA suture material was placed in a plasma reaction chamber with approximately 15-mL reservoir of distilled water to generate the reactive species. The chamber was evacuated to $5 \times 10^{-5}$ Torr, Ar was introduced at a flow rate of approximately 50 sccm, and a chamber pressure of 0.050 Torr was established. The RF power source was switched to the power mode and set to 80 watts. Reactive etching continued for a total of 75 minutes at an operating temperature of approximately 25° C. (room temperature), at which point the power was turned off and the chamber was evacuated to $5 \times 10^{-6}$ Torr. The chamber was allowed to equilibrate to standard atmospheric conditions and the etched PLLA material was removed and was subsequently examined with SEM. In a second experiment, identical procedures are employed to etch a second sample of PLLA suture material except that helium (He) is used in the plasma rather than Ar.

Electron microscopy examination of the PLLA before and after $Ar/H_2O$ plasma etching showed that the original smooth surface of the untreated PLLA was etched to yield a fibrous, loose micro-weave pattern, rather than the filamentous or other micro-morphologies characteristic of metal etching. The porous openings of the woven pattern ranged from 0.25 $\mu$m to 5 $\mu$m in width and 0.5 $\mu$m to 10 $\mu$m in length with approximately 0.1 $\mu$m to 1 $\mu$m diameter strands of PLLA. Pore depths were 0.1 $\mu$m to 15 $\mu$m; pore densities ranged from 0.2 to 15 pores per $\mu m^2$.

EXAMPLE 4

Etching of PLLA with Sputtering of Calcium Phosphate

PLLA is etched with an $Ar/H_2O$ plasma as described in Example 3 simultaneously with a sputtering target of calcium phosphate.

SEM examination of the PLLA sample etched simultaneously with sputtering of calcium phosphate showed that the surface was similarly etched as the PLLA sample in Example 3, but with a distinct increased amount of etching areas per PLLA surface area. The porous openings of the woven pattern ranged from 0.2 $\mu$m to 8 $\mu$m in width and 0.5 $\mu$m to 12 $\mu$m in length with approximately 0.1 $\mu$m to 1 $\mu$m diameter strands of PLLA. Pore depths were 0.1 $\mu$m to 15 $\mu$m; pore densities ranged from 0.2 to 15 pores per $\mu m^2$.

EXAMPLE 5

Plasma Power Modulation

This example demonstrates how the inventive method's etching process can be altered to create additional surface morphologies by slowly varying the input energy to the RF generator via discrete manual changes, at fixed intervals, and returning the power to its original level after each interval. One approach that can be used for power modulation is to run through successively higher increases of the original RF wattage at the appropriate intervals (+25%) at 10 minute intervals), up to a maximum of 100% over nominal wattage, holding this wattage for a previously specified period (5 minutes), at which time the wattage is returned to the original operating conditions.

A metal target item (tantalum wire) is pre-cleaned with a series of sonication steps using various organic solvents and distilled water rinses, then oven dried, and placed in a plasma reaction chamber which is subsequently evacuated to $5 \times 10^{-5}$ Torr. Following the evacuation step, an oxygen plasma is generated for 5 minutes to remove any residual organic material in the chamber. $O_2$ plasma conditions are as follows: $O_2$ pressure at 200 Torr and a RF power level at 150 watts. Chamber temperature is kept at approximately 25° C. (room temperature) throughout the process.

An initial oxide breakthrough procedure is performed to remove the previous cleaning step's oxide formation on the Ta target followed by a reactive ion etching step. The oxide breakthrough step uses a mixture of $BCl_3$ at 20 standard cubic centimeters per minute (sccm), $Cl_2$ at 10 sccm and He at 30 sccm with a chamber pressure of 0.05 Torr. The RF generator is operated in the voltage mode with a sheath voltage between the plasma and metal target set at 300 V; the RF power level initially is set at 200 watts. Breakthrough is allowed to occur for 30 seconds.

In the reactive etching step, the mixing ratio of reactive gases is changed: $BCl_3$ flow rate is decreased to 15 sccm, $Cl_2$ is increased to 10 sccm and He remains at 30 sccm. The chamber pressure is dropped to 0.04 Torr. The RF power source is switched to the power mode and initially set to 100 W with a sheath voltage setting of 250 V. Reactive etching continues for a total of 70 minutes.

During etching, the RF power is repeatedly changed. The initial 100 watt RF power level is raised to 125 watts after 10 minutes and held there for 5 minutes. At 15 minutes into the etching process, the RF power is returned to the original 100 watt setting for 10 minutes, at which time the RF power is lowered to 75 watts for 5 minutes. The original 100 watts RF power is reset and held for 10 minutes followed by one more cycle of RF power modulation as described above. The RF power setting for the last 10 minutes of etching is returned to the original 100 watts level.

At the end of the etching process, power is turned off and the chamber is once again evacuated to $5 \times 10^{-5}$ Torr. A final oxygen plasma cleaning step as performed to remove any residual surface hydrocarbon contamination. Conditions are as follows for this last step: $O_2$ pressure at 200 Torr, $O_2$ flow rate at 30 sccm, and a RF power level at 150 watts. The final $O_2$ cleaning continued for 15 minutes, at which point the plasma is turned off, the chamber is allowed to vent to standard atmospheric conditions and the etched item is cleaned by ultrasonic techniques.

EXAMPLE 6

Application of Amino Groups onto a Polymeric Surface

Amines have been covalently grafted onto polymeric substrate surfaces, such as PMMA, as described in U.S. Pat. No. 5,080,924. The current example shows that plasma induced grafting of an amine group can be successful via $N_2/NH_3$ plasma onto the surface of a plate of poly (acrylonitrile/vinyl chloride) [P(AN/VC)], a biocompatible copolymer, that has previously been etched by the inventive method.

A small piece of the biocompatible copolymer, P(AN/VC), is preconditioned with the inventive method. The P(AN/VC) is placed in a plasma reaction chamber with a 15-mL reservoir of distilled water to generate the reactive species. The chamber is evacuated to $5 \times 10^{-5}$ Torr. Argon is introduced at a flow rate of approximately 15 sccm with 30 sccm $O_2$, and a chamber pressure of 0.05 Torr is established. The RF power source is switched to the power mode and set to 50 watts. Reactive etching continues for a total of 30 minutes at an operating temperature of approximately 25° C. (room temperature), at which point the power is turned off and the chamber is evacuated to $5 \times 10^{-5}$ Torr. The chamber was allowed to equilibrate to standard atmospheric conditions. The etched target article is ready to have amine groups grafted onto the micro-sculpted, roughened P(AN/VC) surface.

A mixture of $N_2$ at 15 sccm, $NH_3$ at 30 sccm and Ar at 30 sccm is introduced into the chamber; total pressure of 0.5 Torr is established. The RF power source is switched to the power mode and set to 100 watts. The amine coating process continues for a total of 60 minutes, at an operating temperature of approximately 25° C. (room temperature), at which point the power is turned off and the chamber is evacuated to $5 \times 10^{-5}$ Torr. The chamber is allowed to vent to standard atmospheric conditions and the coated P(AN/VC) sample is removed for testing.

The etched and amine-grafted P(AN/VC) surface is subsequently examined with SEM to determine the surface morphology. Also, the surface is semi-quantitatively tested for the presence of amino groups.

EXAMPLE 7

Poly(L-Lysine) Coating of a Thin Polymer and Thin Metal

Poly(amino acids) are viable bioactive coating materials. They can be used as surface coatings because they are typically made-up of a large selection of amino acids that offer sites capable of bonding small peptides, drugs and promote cross-linking with other groups.

For this example, the inventive method is applied to two materials; one a thin film of poly(L-lactic acid) (2-cm square, 1 mm thick), the other titanium foil (2-cm square, 1 mm thick). Etching is done as described in Example 1 and Example 3.

The etched samples are sterilized and aseptically dipped into sterile 0.5 Molar solutions of poly(L-lysine) and allowed to aseptically air dry. The etched, ploy(L-lysine) samples are then put into tissue culture with fibroblasts and endothelial cells.

EXAMPLE 8

Vascular Prosthetic

The present invention can provide additional options for vascular prosthetic fabrication techniques, especially for the smaller diameter synthetic coronary arteries that currently have a propensity for thrombosis and vascular infections as a result of their substrate materials.

A commercially available DACRON® vascular shunt, that has not been treated with any of the coatings available (i.e., glutaraldehyde-polymerized proteins, aluminum or other substance), is etched by way of the present invention. The prosthetic is made from the copolymer polyethylene terephthalate and is 10 mm in length and is 3.5 mm wide.

The synthetic shunt is placed into the reaction chamber with a reservoir of approximately 15 mL distilled water to generate the reactive species. The chamber is evacuated to $5 \times 10^{-5}$ Torr, argon was introduced at a flow rate of approximately 15 sccm, oxygen at 30 sccm and a chamber pressure of 0.05 Torr was established. The RF power source is switched to the power mode and set to 100 watts. Reactive etching continues for a total of 15 minutes at an operating temperature of approximately 25° C. (room temperature), at which point the power is turned off and the chamber was evacuated to $5 \times 10^{-5}$ Torr. The chamber is allowed to vent to standard atmospheric conditions and the etched DACRON® vascular shunt is then coated with amino groups via plasma grafting techniques as described in Example 6.

The shunt is then removed from the chamber sterilized with 70% ethanol, and aseptically placed into a 0.5 Molar sterile solution of poly(L-lysine) per the procedures described in Example 7. After the shunt has been thoroughly saturated with the poly(L-lysine) solution, the implant device is in vitro loaded with fibroblasts and endothelial cells in a tissue culture medium. After the appropriate cell growth period has passed and the cells have been deemed usable, the shunt is then implanted into the body through the usual by-pass surgical procedures.

Other embodiments of the invention will be apparent to those skilled in the art from a consideration of this specification and example be considered as exemplary only, with the true scope and spirit of the invention being indicated by the folowing claims.

What is claimed is:

1. A method for the production of a random, irregular surface on an article, comprising:

exposing an article having a polymer surface to a plasma comprised of a reactive etching species that etches the surface by producing a volatile reaction product with the substrate and a second species selected to promote dynamic masking of the substrate, said dynamic masking comprising in situ deposition and removal of a species having etching properties different than the substrate, to obtain non-uniform etching of the substrate.

2. The method of claim 1, wherein said second species comprises a plasma species capable of producing a sputtering effect.

3. The method of claim 2, wherein the plasma species is selected from the group consisting of argon, helium and nitrogen.

4. The method of claim 2, further comprising redeposition of ions sputtered from the surface of the substrate.

5. The method of claim 2, further comprising redeposition of said volatile reaction product.

6. The method of claim 2, further comprising deposition of ions onto the surface sputtered from a sputtering target.

7. The method of claim 6, wherein the sputtering target comprises a form of calcium phosphate.

8. The method of claim 1, wherein the second species is a contaminant selected from the group consisting of water vapor, carbon dioxide, dust, particulates and sputtered ions from impurities of the substrate, a holder supporting the article or walls from a chamber housing the article.

9. The method of claim 2 wherein the plasma further comprises a noble gas.

10. A method of preparing an article for use as a medical device having a roughened surface amenable to bioadhesion, comprising;

exposing a polymeric surface of a medical device to a plasma comprised of a reactive etching species that etches the surface by producing a reaction product with the substrate; and removing the reaction products to obtain a surface having random and irregular etched features of greater than about 0.1 $\mu$m in depth.

11. The method of claim 10, wherein the reactive species comprises a species selected from the group consisting of water vapor, oxygen and hydrogen.

12. The method of claim 10, wherein the reactive species comprises a fluorine-containing compound.

13. The method of claim 10, wherein the plasma fuirther comprises ions sputtered from a sputtering target material.

14. The method of claim 13, wherein the sputtering target material comprises a calcium phosphate.

15. The method of claim 10, wherein the medical device is selected from the group consisting of artificial organs, artificial blood vessels and vascular grafts, heart valves, blood oxygenators, catheters, electrodes, and implant wires.

16. The method of claim 1 or 10, wherein the method produces etching features on the surface having a relief depth of greater than about 1 micron.

17. The method of claim 16, wherein the method produces shallow etching features on the surface having a relief depth in the range of about 1–5 microns and deep etching features in the range of about 5–20 microns.

18. The method of claim 1 or 10, further comprising:
chemically modifying the surface of the article to increase adhesion or improve biocompatibility of the article.

19. The method of claim 1 or 10, further comprising:
physical abrasion of the surface after exposure to the plasma.

20. The method of claim 1 or 10, further comprising:
applying a coating to the irregular surface.

21. The method of claim 19, wherein the coating is selected from the group consisting of organic polymers and forms of calcium phosphate.

22. The method of claim 1, wherein the reactive etching species comprises water vapor.

23. The method of claim 1 or 10, wherein the surface comprises a polymer selected from the group consisting of poly(L-lactic acid), poly(glycolic acid) [PGA], polyethylene, polypropylene, polyurethane, polysulphone, poly(tetrafluoroethylene), poly(methyl methacrylate), polyacrylonitrile, polyamide, poly(vinyl chloride), polyacetal and polyester resins.

24. The method of claim 1 or 10, wherein pressure of a chamber housing the article is in the range of 0.01 Torr to about 1 Torr.

25. The method of claim 1 or 10, wherein power levels of the plasma are modulated over fixed intervals.

26. The method of claim 25, wherein the plasma power level is at radio frequencies at 13.56 MHz and harmonic multiples thereof.

27. The method of claim 1 or 10, wherein the article is isothermally or incrementally cooled.

28. The method of claim 1 or 10, wherein the article is isothermally or incrementally heated.

29. The method of claim 1 or 10, wherein the surface is sonicated in situ.

* * * * *

UNITED STATES PATENT AND TRADEMARK OFFICE
CERTIFICATE OF CORRECTION

PATENT NO. : 6,033,582
DATED : March 7, 2000
INVENTOR(S) : Dosuk D. Lee, Atul Nagras, Pramod Chakravarthy, Anthony M. Majahad Page 1 of 2

It is certified that error appears in the above-identified patent and that said Letters Patent is hereby corrected as shown below:

Title page,
Under Referenced Cited, in line U.S. Patent No. 4,533,272, replace "Mears" with -- Sakai --.

Abstract,
Line 5, replace "are" with -- is --.

Column 2,
Line 14, replace "a" with -- as --.

Column 6,
Line 20, replace "1090" with -- 1990 --.

Column 7,
Line 16, replace "Cl-" with -- Cl· --.
Line 25, replace "OH-" with -- OH· -- and "H-" with -- H· --.

Column 8,
Line 53, replace "$10^{-4}$" with -- $10^4$ --.
Line 54, replace "a" with -- as --.

Column 9
Line 9, replace "with in" with -- within --.
Line 24, after "used" insert -- to --.

Column 11,
Line 3, delete second "of the".

Column 12,
Line 44, replace "el. AL" with -- et al. --.

Column 13,
Line 44, replace "been" with -- be --.
Line 51, replace "tetrafluoroethtylete" with -- tetrafluoroethylene --.
Line 54, replace "vinzyl" with -- vinyl --.
Line 57, after "[P (AN/VC" insert -- ) --.

UNITED STATES PATENT AND TRADEMARK OFFICE
CERTIFICATE OF CORRECTION

PATENT NO. : 6,033,582
DATED : March 7, 2000
INVENTOR(S) : Dosuk D. Lee, Atul Nagras, Pramod Chakravarthy, Anthony M. Majahad It is certified that error appears in the above-identified patent and that said Letters Patent is Column 15,
Line 39, replace "In" with -- It --.

Column 17,
Line 13, delete "be".
Line 61, after "result" insert -- of --.

Column 24,
Line 37, replace "ploy" with -- poly --.

Column 25,
Line 17, replace "folowing" with -- following --.

Column 26, claim 13,
Line 8, replace "fuirther" with -- further --.

Column 26, claim 23,
Line 38, after "poly(L-lactic acid)" insert -- [PLLA] --.

Signed and Sealed this

Thirteenth Day of November, 2001

Attest:

NICHOLAS P. GODICI
Attesting Officer    Acting Director of the United States Patent and Trademark Office